United States Patent
Loecher et al.

(10) Patent No.: US 12,266,444 B2
(45) Date of Patent: Apr. 1, 2025

(54) SYNTHETICALLY TRAINED NEURAL NETWORK FOR MRI TAG TRACKING

(71) Applicants: The Board of Trustees of the Leland Stanford Junior University, Stanford, CA (US); The United States Government As Represented By The Department Of Veteran Affairs, Washington, DC (US)

(72) Inventors: Michael Loecher, Santa Monica, CA (US); Daniel B. Ennis, Palo Alto, CA (US)

(73) Assignees: The Board of Trustees of the Leland Stanford Junior University, Stanford, CA (US); The United States Government As Represented By The Department Of Veteran Affairs, Washington, DC (US)

( * ) Notice: Subject to any disclaimer, the term of this patent is extended or adjusted under 35 U.S.C. 154(b) by 374 days.

(21) Appl. No.: 17/152,302

(22) Filed: Jan. 19, 2021

(65) Prior Publication Data
US 2021/0219862 A1 Jul. 22, 2021

Related U.S. Application Data

(60) Provisional application No. 62/963,123, filed on Jan. 19, 2020, provisional application No. 62/963,124, filed on Jan. 19, 2020.

(51) Int. Cl.
*A61B 5/00* (2006.01)
*A61B 5/055* (2006.01)
*A61B 5/11* (2006.01)
*A61B 5/318* (2021.01)
*G06N 3/08* (2023.01)
(Continued)

(52) U.S. Cl.
CPC .......... *G16H 30/40* (2018.01); *A61B 5/0044* (2013.01); *A61B 5/055* (2013.01); *A61B 5/1128* (2013.01);
(Continued)

(58) Field of Classification Search
None
See application file for complete search history.

(56) References Cited

U.S. PATENT DOCUMENTS 6,292,683 B1  9/2001  Gupta
6,934,407 B2  8/2005  Allouche
(Continued)

FOREIGN PATENT DOCUMENTS

WO   WO2020014286 A1 * 7/2019 ............. G06V 10/82

OTHER PUBLICATIONS

Reeder et al. "Tag Contrast in Breath-Hold CINE Cardiac MRI" (Year: 1994).*
(Continued)

*Primary Examiner* — Jeffrey G Hoekstra
*Assistant Examiner* — Gabriel Victor Popescu
(74) *Attorney, Agent, or Firm* — Ballard Spahr LLP

(57) ABSTRACT

A method for magnetic resonance imaging (MRI) tag tracking includes: synthetically generating tagged data from natural images combined with programmed tag motion and a full Bloch simulation; training a convolutional neural network (CNN) with the synthetically generated tagged data to generate grid tag motion paths; acquiring MRI images using a tagged imaging method; inputting the acquired images into the CNN to estimate motion paths of tracked points; and determining from the estimated motion paths a path of tag lines through the cardiac cycle from a set of tagged MRI images. The method can calculate strain curves from the estimated motion paths using $E_{cc}$ derivation.

18 Claims, 11 Drawing Sheets

(51) Int. Cl.
  *G06V 10/44* (2022.01)
  *G06V 10/764* (2022.01)
  *G06V 10/82* (2022.01)
  *G16H 30/40* (2018.01)

(52) U.S. Cl.
  CPC ............ *A61B 5/318* (2021.01); *A61B 5/7267* (2013.01); *A61B 5/7289* (2013.01); *A61B 5/748* (2013.01); *G06N 3/08* (2013.01); *G06V 10/454* (2022.01); *G06V 10/764* (2022.01); *G06V 10/82* (2022.01); *A61B 2576/023* (2013.01)

(56) References Cited

U.S. PATENT DOCUMENTS

| | | | | |
|---|---|---|---|---|
| 11,393,092 | B2* | 7/2022 | Sun | G06T 7/0014 |
| 2020/0160122 | A1* | 5/2020 | Lints | G06T 3/40 |
| 2021/0133510 | A1* | 1/2021 | Boulanger | G06V 10/82 |

OTHER PUBLICATIONS

Moore et al. "Calculation of Three-dimensional Left Ventricular Strains from Biplanar Tagged MR Images" (Year: 1992).*
Tran et al. "(2+1)D Convolution" (Year: 2018).*
Lui et al. "CoordConv" (Year: 2018).*
Ronneberger, O., Fischer, P. & Brox, T. U-net: Convolutional networks for biomedical image segmentation. in Lecture Notes in Computer Science (including subseries Lecture Notes in Artificial Intelligence and Lecture Notes in Bioinformatics) 9351, 234-241 (Springer Verlag, 2015).
Nam, H. & Han, B. Learning Multi-domain Convolutional Neural Networks for Visual Tracking. in Proceedings of the IEEE Computer Society Conference on Computer Vision and Pattern Recognition Dec. 2016, 4293-4302 (2016).

* cited by examiner

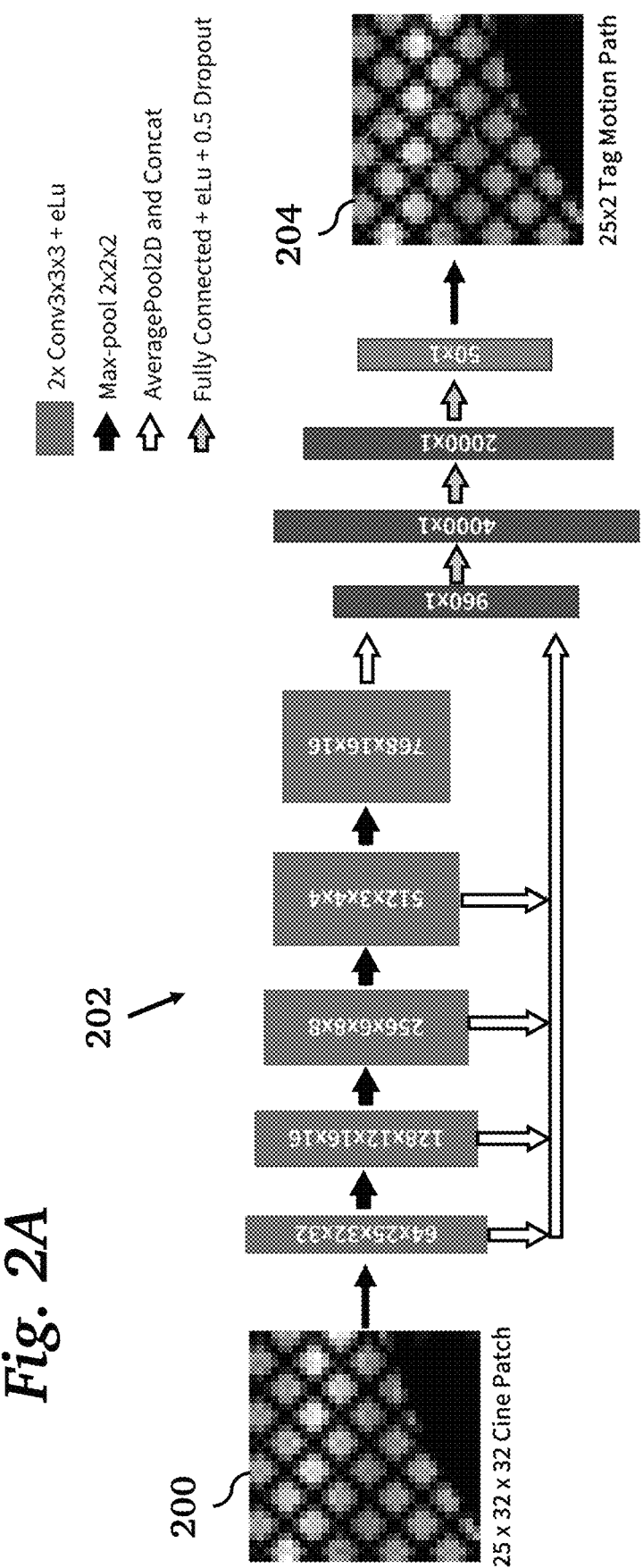
*Fig. 2A*
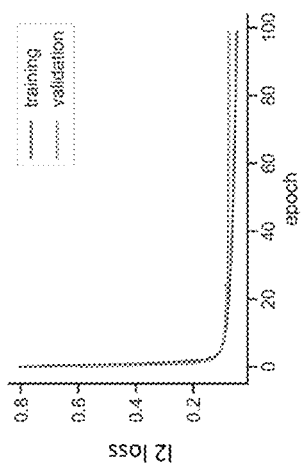
*Fig. 2B*
*Fig. 2C*

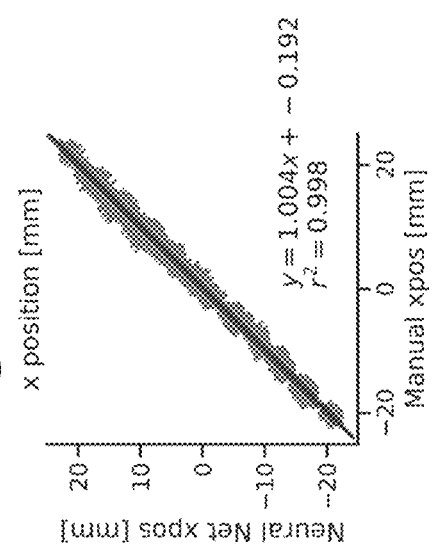
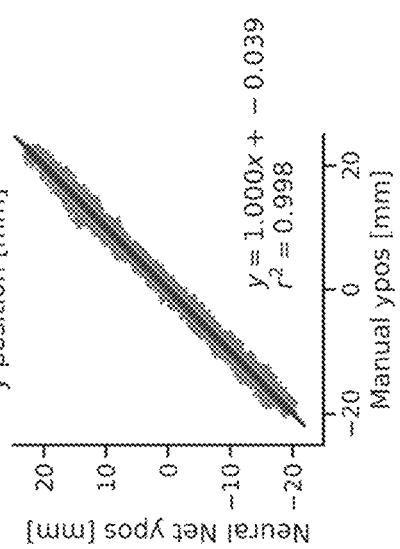
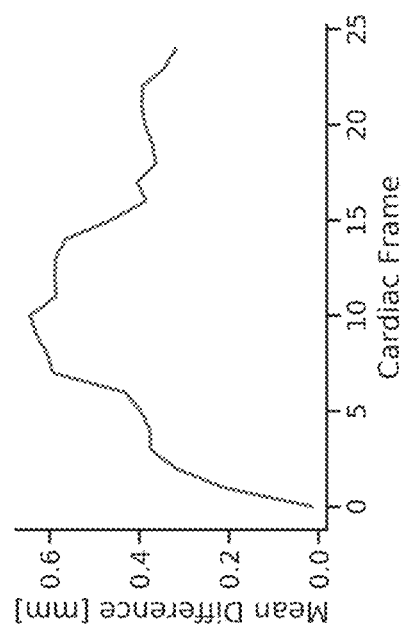
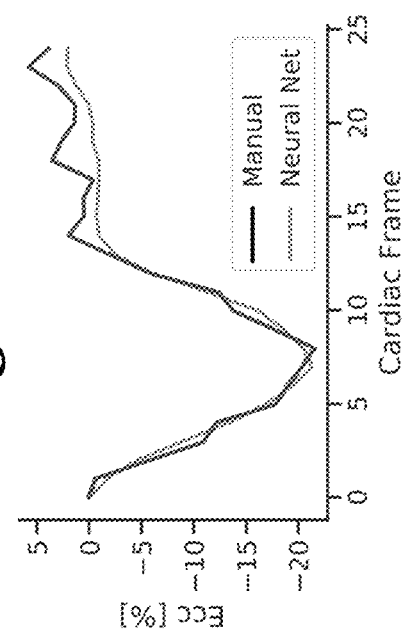
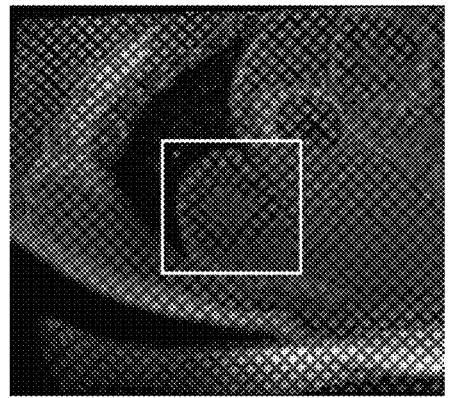
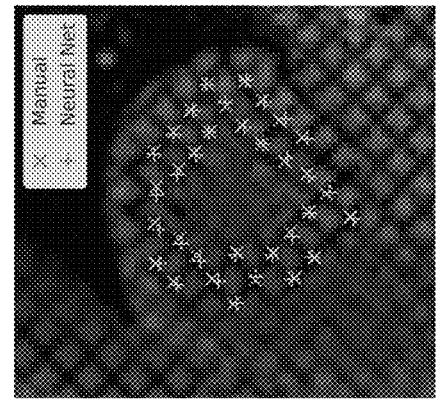

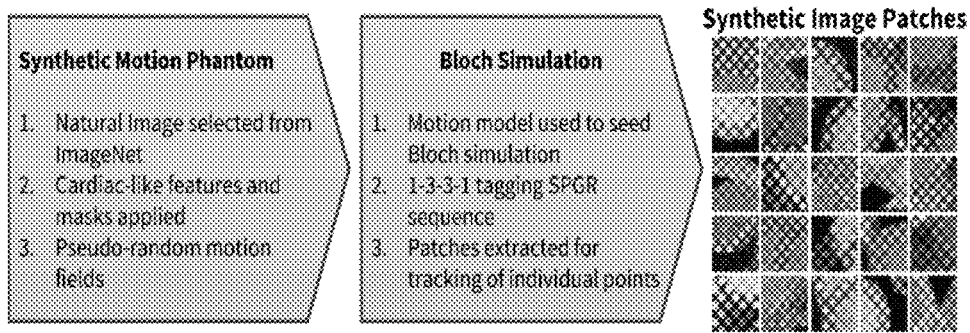
*Fig. 5A*
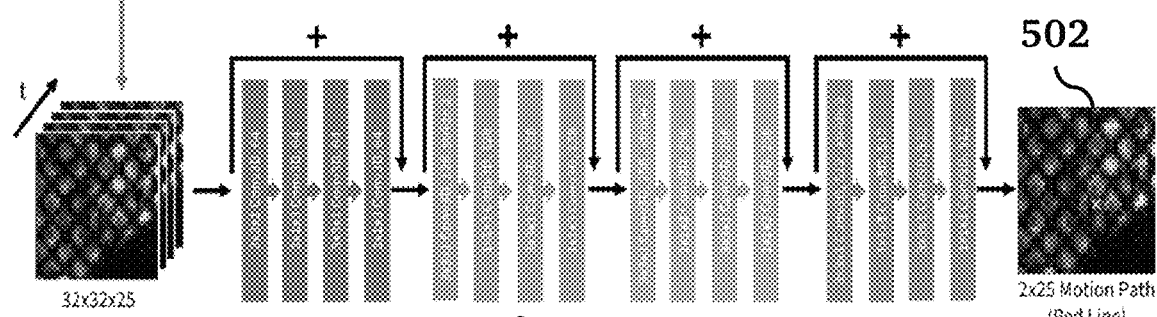
*Fig. 5B*
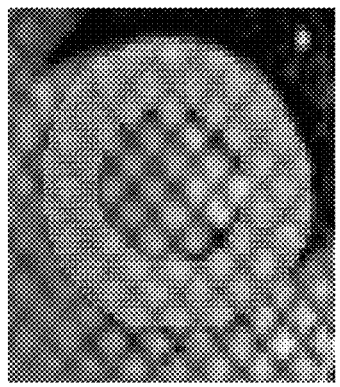 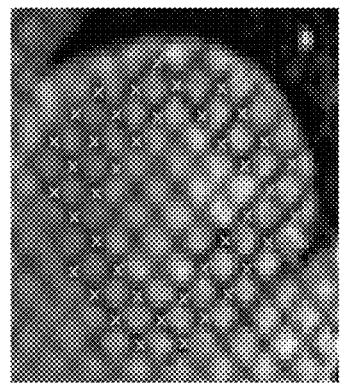
*Fig. 5C*     *Fig. 5D*

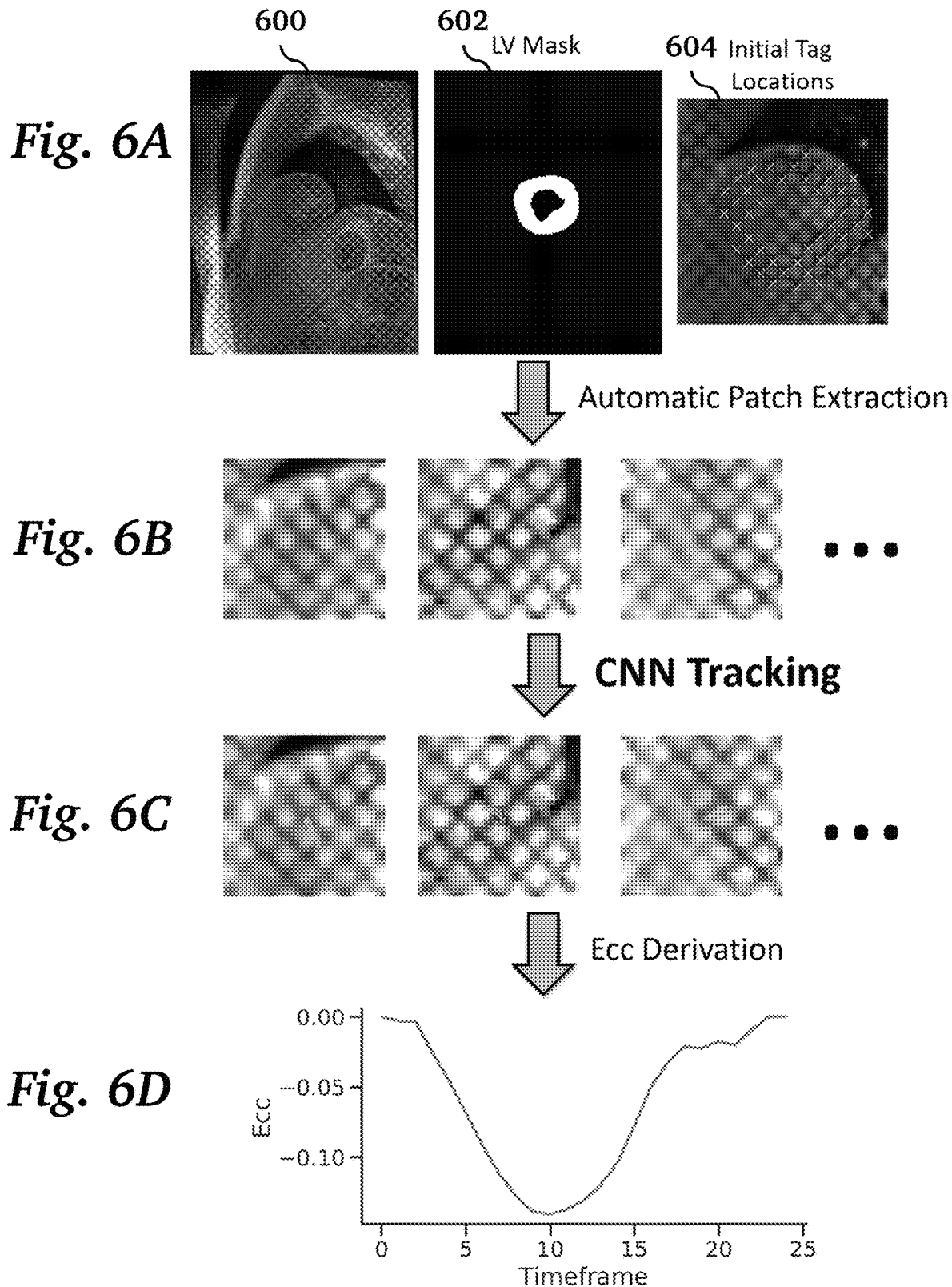

SYNTHETICALLY TRAINED NEURAL NETWORK FOR MRI TAG TRACKING

CROSS-REFERENCE TO RELATED APPLICATIONS

This application claims priority from U.S. Provisional Patent Application 62/963,123 filed Jan. 19, 2020, and from U.S. Provisional Patent Application 62/963,124 filed Jan. 19, 2020, both of which are incorporated herein by reference.

FIELD OF THE INVENTION

The present invention relates generally to medical imaging. More specifically, it relates to techniques for magnetic resonance imaging tag tracking.

BACKGROUND OF THE INVENTION

Quantitatively understanding the motion of the heart is a useful tool in diagnosing and planning treatment of cardiac disease. One common method to do this is with magnetic resonance imaging (MRI). However, the most common method (Tagging MRI) is currently limited by complicated, and potentially error-prone, post-processing tracking methods.

Cardiac MRI (CMR) tagging enables the quantitative characterization of global (e.g., torsion) and regional cardiac function (e.g., strain), but its clinical adoption has long been hampered by painful post-processing methods. Despite the challenge of extracting the information, these quantitative measurements are important for understanding cardiac dysfunction, evaluating disease progression, and characterizing the response to therapy.

There are numerous other existing methods. One common method being used is called HARP (Harmonic Phase). This method uses a tight frequency filter to extract displacement values. Although this method is easy to use, it drastically lowers imaging resolution, and can still be corrupted by other echoes (raw MRI signals) in the data. To partially address the echo corruption, two sets of data can be acquired, doubling scan time, but this only provides marginal benefits.

Although numerous methods for tracking tags exist [1-4], many include laborious segmentation and tag-tracking corrections, or other substantial user input. Convolution neural networks (CNN) might be considered for imaging segmentation [5] and motion tracking [6]. Training a CNN, however, requires: 1) a large amount of training data; and 2) the associated 'ground truth' tag motion. These are not readily available.

Other purely image-based approaches exist to track the tag lines. These, however, often need manual supervision, take a long time to compute, and/or do not behave well in the presence of noise, artifacts, nor after tag lines have significantly faded (which is an unavoidable consequence of MRI physics).

Another style of existing method are methods such as DENSE (Displacement encoding via stimulated echoes), make the post-processing easier by acquiring additional imaging data. However, this requires much longer scan times, or a drop in imaging resolution to make up for the scan time, resulting in lower quality images, or clinically unreasonable scan times.

BRIEF SUMMARY OF THE INVENTION

The present inventors have developed a technique to leverage machine learning to solve this problem automatically, quickly and reliably.

To address the usability and accuracy problems faced by current tag tracking algorithms, the inventors developed a convolutional neural net (CNN) based approach to determining the path of tag lines through the cardiac cycle from a set of tagged MRI images. This type of approach previously would have been limited by the need for large amounts of training data, and the associated ground truth motion paths. The inventors addressed this issue by creating an extensive synthetic data generation and simulation framework. The approach generates a large amount of synthetically tagged data from natural images combined with programmed tag motion and a full Bloch simulation. These images are then used to train a neural network to generate grid tag motion paths from the input images.

A principal application of this technique is the postprocessing of cardiac tagged MRI, but this could be extended to other motion fields measured with tagged MRI outside the heart.

In one aspect, the invention provides a method for magnetic resonance imaging (MRI) tag tracking, the method comprising: synthetically generating tagged data from natural images combined with programmed tag motion and a full Bloch simulation; training a convolutional neural network (CNN) with the synthetically generated tagged data to generate grid tag motion paths; acquiring MRI images using a tagged imaging method; inputting the acquired images into the CNN to estimate motion paths of tracked points; and determining from the estimated motion paths a path of tag lines through the cardiac cycle from a set of tagged MRI images. Preferably, the convolutional neural network (CNN) includes both coordinate convolutions and (2+1)D convolutions. The method may include calculating strain curves from the estimated motion paths using strain tensor derivation. The method may include applying tagging pulses asynchronously with an ECG trigger, and including a time-from-tagging sampling dimension in tagged data.

BRIEF DESCRIPTION OF THE SEVERAL VIEWS OF THE DRAWINGS

FIG. 2A shows a CNN architecture used to generate x and y positions of the tag motion paths from input tagged images, according to an embodiment of the invention.

FIG. 2B shows details of the network architecture and the training process, according to an embodiment of the invention.

FIG. 2C is a graph that shows loss functions for the training process by epoch, according to an embodiment of the invention.

FIG. 4A shows an example of the in vivo images used for testing, according to an embodiment of the invention.

FIG. 4B shows an overlay of the CNN identified tag locations and manually identified tag locations, according to an embodiment of the invention.

FIG. 4C is a graph that shows the mean difference between CNN and the manually tracked tag locations, according to an embodiment of the invention.

FIG. 4D is a graph that shows the $E_{cc}$ curves for the CNN and manually tracked tag locations, according to an embodiment of the invention.

FIGS. 4E-F show linear regressions of CNN and the manually tracked x and y positions, respectively, from all points and all timeframes, according to an embodiment of the invention.

FIG. 5A, which shows an overview of the synthetic data generation and the output image patches used for training, according to an embodiment of the invention.

FIG. 5B shows an 18-layer Resnet architecture with modifications to include both coordinate convolutions and (2+1)D convolutions, according to an embodiment of the invention.

FIG. 5C and FIG. 5D show the points tracked for the voxel-wise and intersection techniques, respectively, according to an embodiment of the invention.

FIGS. 6A-D show an overview of the processing workflow, according to an embodiment of the invention.

DETAILED DESCRIPTION OF THE INVENTION

In on embodiment of the invention, a CNN approach was developed for fast and automatic tag tracking. To train the network, we used an extensive data generation and simulation framework. The approach generates a large amount of synthetically tagged data from natural images combined with programmed tag motion and a full Bloch simulation. These images are then used to train a neural network to generate grid tag motion paths from the input images.

Synthetic data is generated by randomly selecting a natural image from any database of images. The image is discretized into a point cloud, with multiple points per image pixel. These points are assigned motion paths with addition perturbations, to create physiological or non-physiological motion fields. Each point is also assigned a T1 and T2 relaxation time constant from a randomly generated curve. A mask on image intensity, as well as oval masks, are randomly applied to better simulated air-tissue interactions. These points are then put through a Bloch simulation to create a realistic looking MR images that mirror the physics of a traditional tagging acquisition. Random noise is added to the images as well.

The synthetic training data generator quickly generates MR-like images of natural objects that have defined motion paths, air cavities, relaxation, and imaging artifacts randomly selected from a set of physiologically reasonable values. These are used to train a convolutional network designed within our group that has shown to be robust to noise and other artifacts.

The network is trained by generating approximately 600,000 training datasets using the described data generator. The true motion paths are known from the generation, which are used for the truth data. The data is trained with a mean squared error loss function comparing the predicted motion path for a point to the true motion path. 100 epochs of training are run with an ADAM optimization scheme.

Finally, the motion paths from the training data are entered into a strain calculation algorithm to derive the final clinically relevant parameters.

Strain is calculated from the predicted motion paths using a conventional method using the relative displacement of the point positions.

As this uses neural networks, we use common libraries to fit the training data to the network.

Synthesis of Motion Field Training Images

Figure 1A:
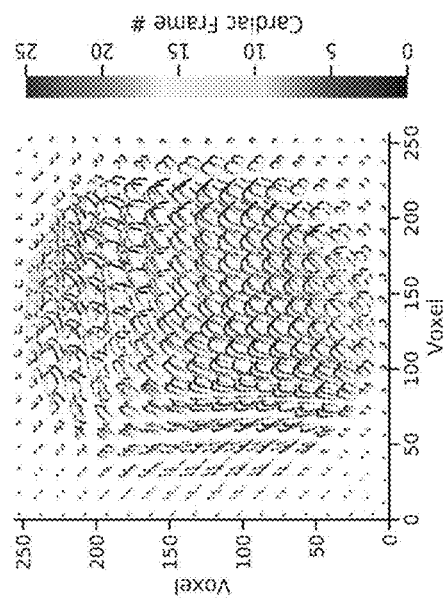
FIG. 1A shows a natural image used to develop a training database, according to an embodiment of the invention.
Figure 1B:
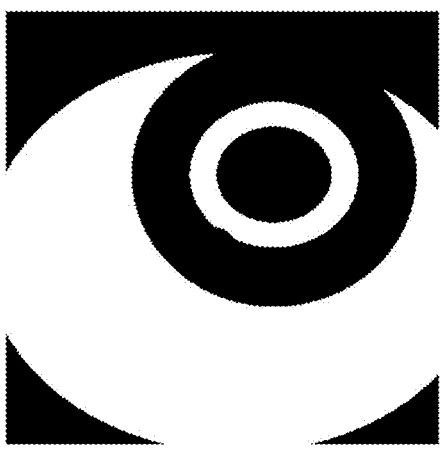
FIG. 1B shows a random annular mask applied to the natural images to develop a training database, according to an embodiment of the invention.
Figure 1C:
FIG. 1C shows periodic motion fields coded by cardiac time frame applied to the natural images to develop a training database, according to an embodiment of the invention.
Figure 1D:
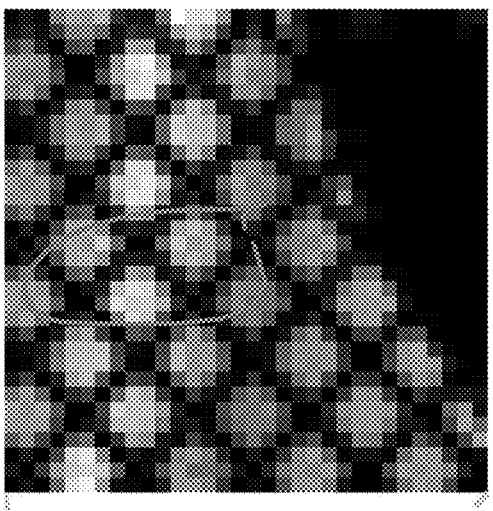
FIG. 1D shows T1 and T2 curves generated from random polynomials used for Bloch simulation, according to an embodiment of the invention.
Figure 1E:
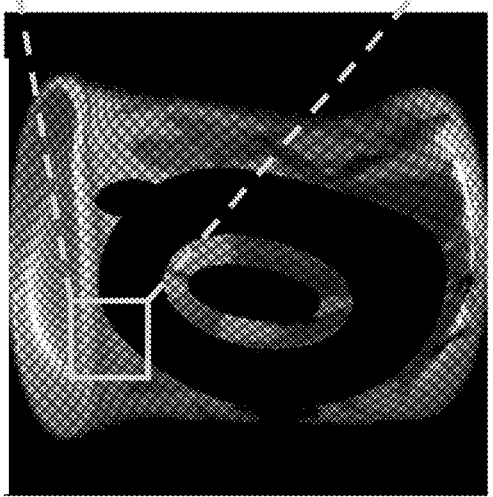
FIG. 1E shows output from a simulated tagging sequence used to develop a training database, according to an embodiment of the invention.
Figure 1F:
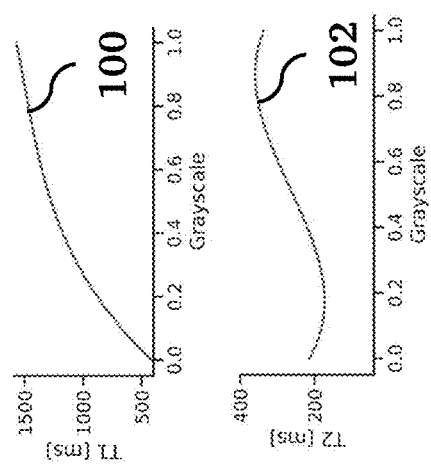
FIG. 1F shows a patch extracted for a single tag location, and the defined motion path used to develop a training database, according to an embodiment of the invention.

In one illustrative example, images were randomly selected from a database of natural images. FIG. 1A shows an example of one such natural image used to develop the training database. Random annular masks, such as the annular mask shown in FIG. 1B, and periodic motion fields coded by cardiac time frame, such as shown in FIG. 1C were applied to the natural images. The motion fields were generated with a set of randomly generated parameters describing an ellipse shape, as well as an additional 2nd order polynomial on the x and y positions of the path. T1 and T2 values were also randomly assigned by mapping gray-scale values on a 3rd order polynomial with random parameters, as shown in the graphs of FIG. 1D, which shows T1 and T2 curves 100, 102 generated from random polynomials used for Bloch simulation. These dynamic training images were used as the input to a Bloch simulation that generated tagged images of the moving objects, as illustrated in FIG. 1E, which shows the output from the simulated tagging sequence (frame 8 from a 25 frame series). The simulation added complex gaussian noise (SNR=10-50), and grid tag spacing=4-12 mm, and a 256×256 image matrix with 25 timeframes. The images were cropped to a 32×32 voxel patch dataset with 25 timeframes, centered around the tag location to be tracked at t=0. The analytic 'ground truth' tag motion paths were used for training, as illustrated in FIG. 1F, which shows a patch from FIG. 1E that was extracted for a single tag location, and the defined motion path used for training.

The method may be implemented as a complete post-processing chain. After acquiring the images with a conventional tagged imaging method, the images are loaded, and the method applies the tag tracking algorithm, estimates myocardial motion patterns, and calculates a relevant quantitative parameter, e.g., cardiac strain. Post-processing may be used to select the myocardial tissue in the first time frame. The method then completes the tag tracking with a CNN, and calculates strain or other parameter from those paths automatically.

This method can be used for all post-processing of these images. It can make the processing convincingly easier, therefore it could lead to more of these images being used clinically, as the current cumbersome post-processing steps are one of the limiting factors to adoption.

Computational Cardiac Phantom

In the example illustration, a trained network was tested on synthetic cardiac MR images generated using a computational deforming cardiac phantom [7]. The trained CNN was compared to both the 'ground truth' tag locations and strain values. The performance was measured for a range of SNR values by comparing RMSE of the tag locations and the error in peak mid-wall circumferential strain ($E_{cc}$).

In Vivo Data

Tagging data from healthy pediatric volunteers (N=5, median age=15Y) was analyzed with the trained CNN. $E_{cc}$ values were calculated from the detected tag locations. Tag motion paths and strains computed using the CNN were compared to the ones from manually tracked tag locations.

Results

Details of the training process are shown in FIGS. 2A-C wherein 600,000 unique synthetic tag patches were generated and used for training. FIGS. 3A-D show example images from the computational deforming cardiac phantom, as well as an overlay of our CNN calculated tag locations. RMSE of the tag locations was <0.4 mm for SNR>10, and strain differences were <0.02. Very good agreement was seen in vivo between the CNN tagging and manual tag tracking (FIG. 4). Tag locations were <1.0 mm apart and strain values of the cardiac cycle agreed to within 0.02 $E_{cc}$.

In more detail, FIG. 2A shows the CNN architecture used in this example embodiment. The cine patch image 200 is used as input, and is followed by a standard CNN 202 with 3D convolutions. The weights from the CNN are finished in three fully connected layers before outputting the x and y positions of the tag motion path 204. FIG. 2B shows details of the network architecture 202 and the training process. FIG. 2C is a graph that shows loss functions for the training process by epoch.

Figure 3A:
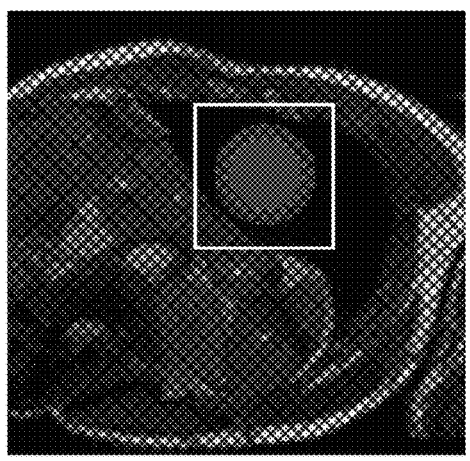
FIG. 3A shows an example of the computational deforming cardiac phantom, according to an embodiment of the invention.
Figure 3B:
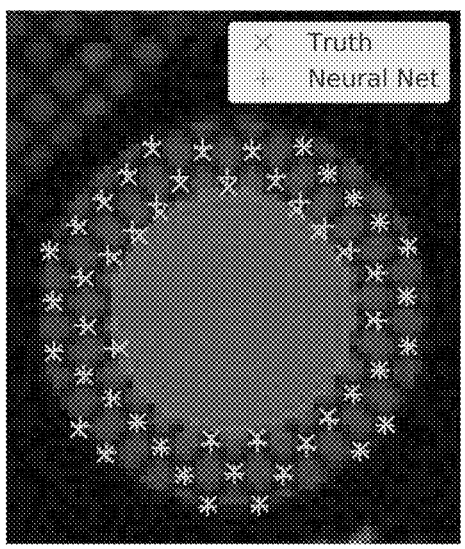
FIG. 3B shows an overlay of the CNN identified tag locations compared to 'ground truth', according to an embodiment of the invention.
Figure 3C:
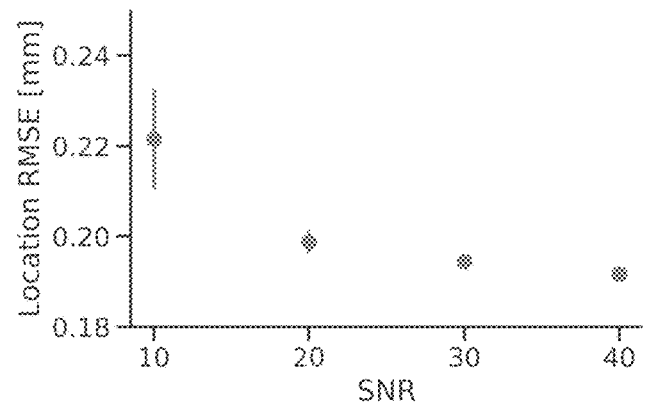
FIG. 3C shows a plot of the RMSE of tag locations in relation to SNR, tested over 10 trials, according to an embodiment of the invention.
Figure 3D:
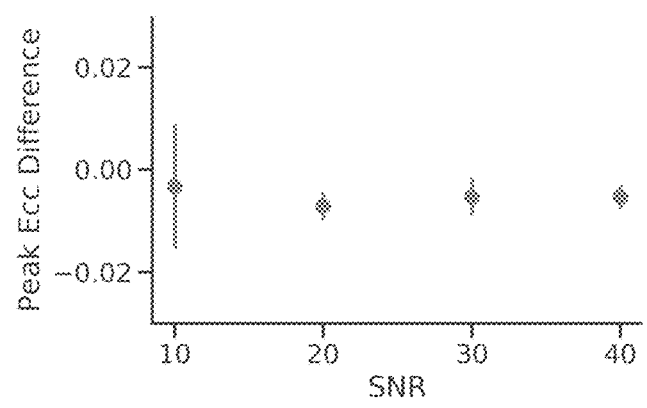
FIG. 3D shows a plot of the error in peak $E_{cc}$, compared to ground truth, according to an embodiment of the invention.

FIG. 3A shows an example of the computational deforming cardiac phantom. FIG. 3B shows an overlay of the CNN identified tag locations marked with + compared to 'ground truth' marked with x. FIG. 3C shows a plot of the RMSE of tag locations in relation to SNR, tested over 10 trials. FIG. 3D shows a plot of the error in peak $E_{cc}$, compared to ground truth.

FIG. 4A shows an example of the in vivo images used for testing. FIG. 4B shows an overlay of the CNN identified tag locations marked with + and manually identified tag locations marked with x. FIG. 4C is a graph that shows the mean difference between CNN and the manually tracked tag locations. FIG. 4D is a graph that shows the $E_{cc}$ curves for the CNN and manually tracked tag locations. FIGS. 4E-F show linear regressions of CNN and the manually tracked x and y positions, respectively, from all points and all timeframes.

Discussion

In this illustrative example, a CNN was used to very quickly (<1 s) and reliably track tag motion paths for the calculation of strains. The CNN was entirely trained using natural images with simulated motion paths and Bloch simulated tagging. By creating large amounts of training data with known displacement paths, the network can easily be retrained without the need to acquire large amounts of new training data and postprocess it. A computational deforming cardiac phantom with known strains was used to validate that the method works well for standard clinical SNR levels and resolutions. In vivo results showed very good agreement in tag motion paths, as well as calculated strains, compared to locations measured manually by an expert. Other embodiments and experiments may incorporate the cardiac phantom into the training process, test the effect of adding real data into the training, combine segmentation into the network, and demonstrate use on a larger cohort with pathologies.

We now discuss experiments that demonstrate and evaluate the feasibility of using a convolutional neural net (CNN) based tag tracking algorithm for deriving strain measurements in grid tagged cardiac MR images. The method was tested in 23 subjects. When compared to commercial software, the CNN-based method produces similar measurements for peak $E_{cc}$ and shows lower strain in boys with DMD compared to healthy subjects. Peak $E_{cc}$ was not significantly different within cohorts when compared between methods.

Introduction

Duchenne Muscular Dystrophy (DMD) is a fatal inherited genetic disorder, causing muscle degeneration that eventually leads to respiratory and/or heart failure [8]. Cardiomyopathy is a significant factor in the morbidity and mortality of the disease, and cardiac MRI (CMR) has become an important clinical tool used to follow the progression of the disease and plan appropriate treatment [9].

Measures of cardiac function using left ventricular ejection fraction (LVEF) is a routine biomarker for staging and predicting cardiac outcomes in boys with DMD [10]. Cardiac strain has also been suggested to be a useful biomarker, and has been shown to provide earlier insight and better distinguish DMD hearts from healthy hearts compared to LVEF [11].

While strain measurements appear to be a useful biomarker for studying DMD cardiomyopathy, deriving strain from CMR tagged images is labor intensive. Tracking tag lines through the cardiac cycle measures the myocardial motion, from which strains can be calculated. In this illustrative experimental example, we investigate the use of CNN based tag tracking algorithm for following tag lines through the cardiac cycle, and compare it to a commercially available method in a cohort of boys with DMD and healthy volunteers. The CNN method requires little user input, and has been trained and validated on synthetic data with known truth. This has increased tag tracking accuracy and ease-of-use.

Methods

With a cine tagged cardiac image as input and initial tag locations in the myocardium at t=0, the method solves for tag motion paths throughout the cardiac cycle for each tag point. To improve computational efficiency the image is automatically cropped to a patch for each tag location to be tracked. The CNN was previously trained on synthetically generated data covering a wide range of possible motion paths, underlying object shapes, relaxations, noise, and tagging properties. The tag motion paths were then used to derive circumferential strains ($E_{cc}$) in a mask of the LV [12]. The $E_{cc}$ values measured with the CNN were compared to a traditional method from commercial software (Diagnosoft, Myocardial Solutions).

A synthetic data generation algorithm was used to generate time-resolved deforming natural images for training with known displacement values for all points and timeframes. This data generator then uses a Bloch simulation to produce a cine grid tagged dataset of synthetic image patches 500 with realistic image quality, as detailed in FIG. 5A, which shows an overview of the synthetic data generation and the output image patches used for training. The images and their respective motion paths were used to train an 18-layer Resnet architecture, shown in FIG. 5B, with modifications to include both coordinate convolutions and (2+1)D convolutions, therefore enabling convolutions in both the spatial and temporal dimensions. The network tracks a single point from a surrounding 32×32 voxel patch. Each individual point to be tracked is processed by the network to extract its specific motion path as output 502 each being 2×25 motion displacements (x, y per timeframe). One million training patches 500 were used to train the network, and inference takes ~1 second to track all voxels in a time-resolved series.

In an experimental test, the methods were applied in short-axis, mid-LV slices in healthy pediatric subjects (N=9) with IRB approval and consent. Cine grid tagged images were acquired with: TE/TR=2.5 ms/4.9 ms, flip angle=10°, FOV=260 mm×320 mm, 110° total tagging flip angle, spatial resolution 1.4 mm×1.4 mm×8 mm, 25 time frames, 8-12 s breath hold. FIG. 5C and FIG. 5D show the points tracked for the voxel-wise and intersection techniques, respectively. The LV was manually segmented in the first time frame and all voxels in the mask were used for subsequent automated tracking, and shown in FIG. 5C. Additionally, the tag line intersections were manually delineated and tracked with a separate network trained only on intersection tracking for comparison, as shown in FIG. 5D. This approach has been well validated for accurately tracking tag line intersections, as well as computing $E_{cc}$.

Tracked points were visualized with displacement vectors, as well as displacement maps, which were generated by linearly interpolating the tracked points onto an imaging grid. Strains were calculated by differentiating the displacement field interpolated using a radial basis function with a Gaussian kernel and shape parameter=1.4 mm (1 pixel) for voxel tracking and 8 mm (equivalent to tag spacing) for tag line intersection tracked images. Circumferential ($E_{cc}$) and radial ($E_{rr}$) strains were investigated as maps, as well as the mean global strain values across the LV ROI.

FIGS. 6A-D show an overview of the processing workflow. The cine image series 600, LV mask 602, and initial tag locations 604 (FIG. 6A) are given as input. Automatic patch extraction is used to extract patches centered at each tag location (FIG. 6B). The extracted patches are fed through the CNN, which outputs the motion path of that initial tag location (FIG. 6C). The motion paths are then used to calculate strain curves (FIG. 6D) by $E_{cc}$ derivation.

14 patients (median age=14Y) and 9 healthy controls (median age=15Y) underwent a CMR exam including a mid-ventricular gridded tagged acquisition (spatial resolution=1.4×1.4×8 mm, TE/TRes=2.12/24-48 ms, 25 retrospectively binned phases, grid tag spacing=8 mm). Subjects were imaged at either 1.5T or 3T (Siemens Avanto or Skyra).

After computing $E_{cc}$ curves for all subjects with both methods (CNN and conventional), we compared peak $E_{cc}$ with Bland-Altman plots, and temporally resolved $E_{cc}$ curves. Additionally, the peak mid-wall $E_{cc}$ of both cohorts was measured and compared.

Results

Figure 7B:
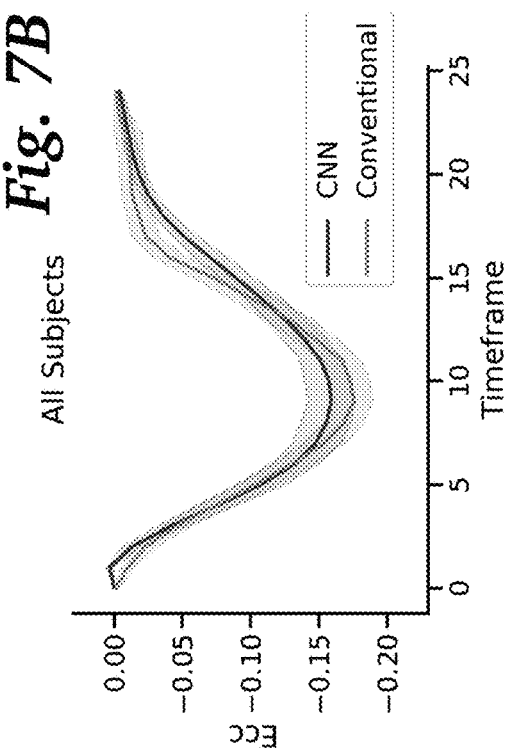
FIG. 7B-D show line plots of the time resolved $E_{cc}$ averaged over a given subject population, according to an embodiment of the invention.
Figure 7D:
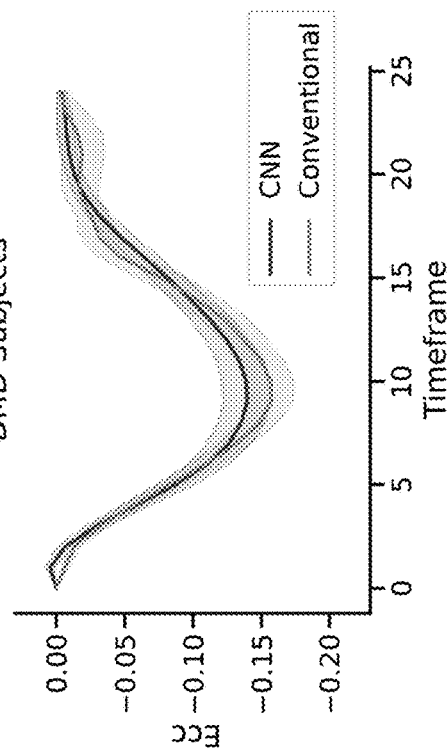
Figure 7A:
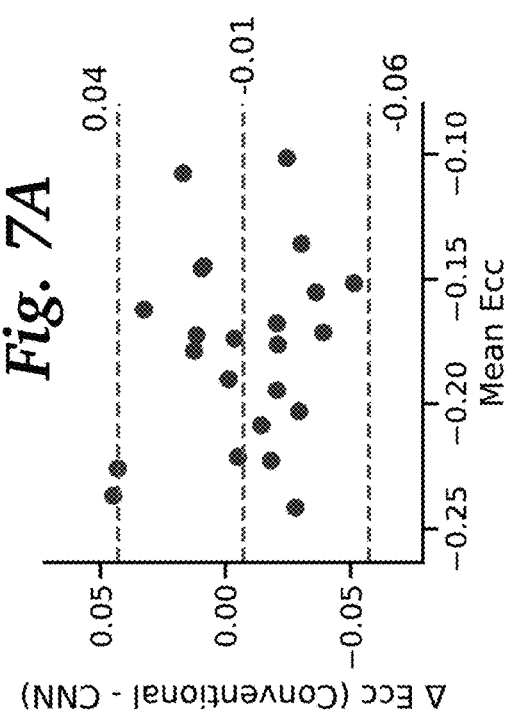
FIG. 7A shows a Bland-Altman plot comparing the peak mid-wall $E_{cc}$ values measured for each subject, comparing both methods, according to an embodiment of the invention.
Figure 7C:
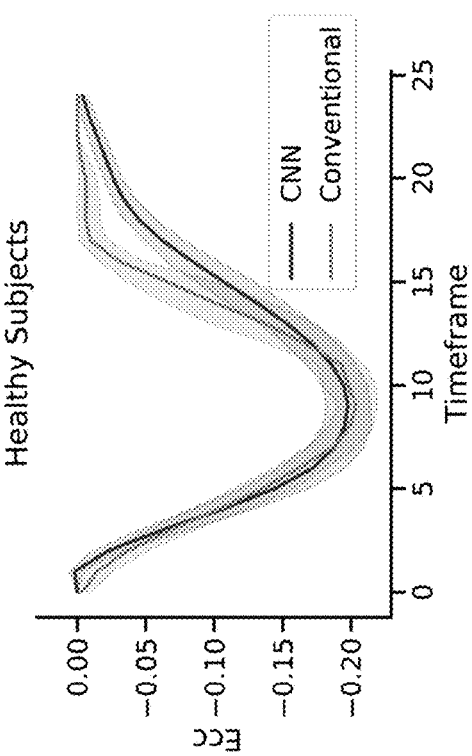

FIG. 7A shows a Bland-Altman plot comparing the peak mid-wall $E_{cc}$ values measured for each subject, comparing both methods. A bias of −0.01 was seen with a −0.06 to 0.04 confidence interval (1.96×SD). The difference between methods within cohorts was not significant [DMD cohort: p=0.32 t-test, Healthy cohort: p=0.99 t-test]. FIG. 7B-D show line plots of the time resolved $E_{cc}$ averaged over a given subject population. FIG. 7B shows the mean time resolved $E_{cc}$ curve for all subjects calculated with both methods, FIG. 7C shows healthy subjects and FIG. 7D shows boys with DMD. The shaded areas in the line plots represent the bootstrapped 95% confidence interval. Good agreement was seen between the curves, especially during the first ~⅔ of the cardiac cycle.

Both methods show a significant (p<0.001 t-test) difference in $E_{cc}$ between the cohorts.

Figure 8A:
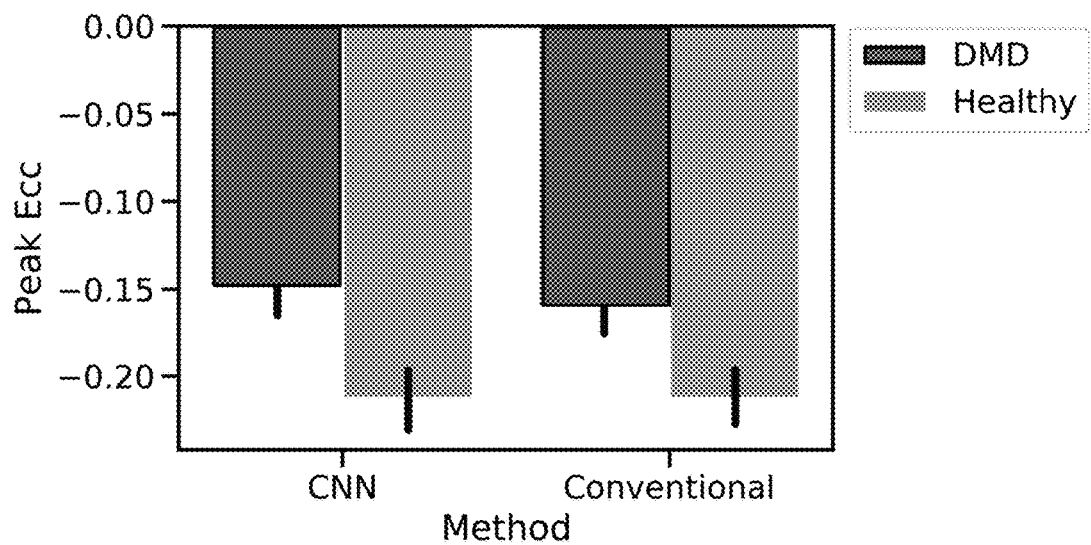
FIGS. 8A-B show Bar plots of the peak mid-wall $E_{cc}$ values calculated with both methods, for healthy subjects and boys with DMD, according to an embodiment of the invention.
Figure 8B:
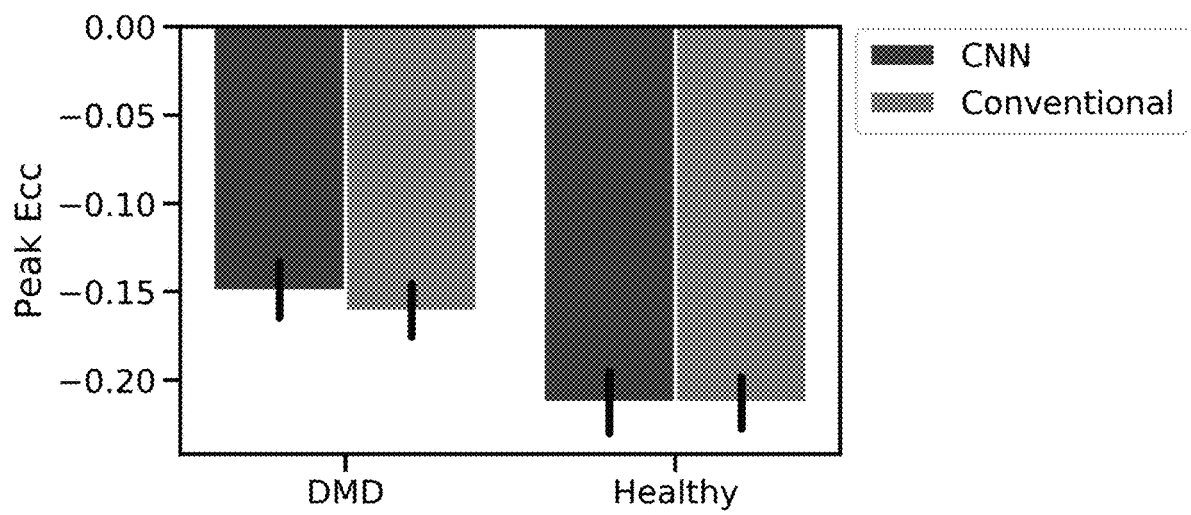

FIGS. 8A-B show Bar plots of the peak mid-wall $E_{cc}$ values calculated with both methods, for healthy subjects and boys with DMD. Error bars represent the bootstrapped 95% confidence interval. FIG. 8A shows paired cohorts, and FIG. 8B shows paired methods, both with the same data. Both methods show a significant (p<0.001 t-test) difference in $E_{cc}$ between the cohorts.

Discussion

This work shows the use of a CNN based tag tracking algorithm and its effectiveness in a population of boys with DMD and healthy controls. Good agreement between the strain measures was seen in the cohorts as a whole for peak $E_{cc}$ and for temporally resolved $E_{cc}$, but larger differences were apparent late in the cardiac cycle. Careful inspection of subject-specific differences showed that improvements in the CNN may still be needed. These differences may be due to the tag tracking methodology, or other choices in the workflow such as different definitions of mid-wall, segmentation differences, or differences in the strain computation. Other embodiments may include comparing multiple tag tracking workflows and carefully controlled comparisons of specific aspects of the workflow. Additionally, other embodiments may automate the initial selection of tag points at t=0, as well as segmentation, to make the strain calculations fully automated.

Asynchronous Tagging

Tagging MRI is a powerful tool for quantitatively assessing the performance of the heart as it beats in vivo. However, the method is hindered by a drop in performance as the cardiac cycle progresses, leading to reduced data quality during cardiac relaxation and diastole. We address this issue by providing a MRI pulse sequence that tags the cardiac tissue at various times in the cardiac cycle, which enables producing uniform tag quality for all time frames.

Cardiac MR tagging sequences traditionally apply a short series of radiofrequency (RF) pulses immediately after the ECG trigger. These tag pulses produce saturated lines in the magnitude images (grid-tagged) or encode displacement values directly into the complex phase (DENSE). The tagged images are acquired with a k-space segmented cine spoiled gradient echo (SPGR) imaging sequence over the course of several heart beats. The tagging pattern, however, fades due to T1-relaxation and the encoded information is slowly lost as the images are acquired. This leads to good tag quality during cardiac contraction (systole), but poorer quality data during filling (relaxation), and often unusable data quality during diastasis, all of which contain important information about cardiac function.

The methods that exist to deal with this problem all require additional scan time, and more importantly, only partially alleviate the problem.

The primary method used to decrease tag fading is to use a technique called Complementary SPAtial Modulation of Magnetization, which doubles the scan time required to acquire tagged images. This in turns allows for a second dataset to be acquired with the tagging pulse 180 degrees out of phase with the first, which when combined make the tag lines appear to persist longer. This technique, however, requires double the scan times, requires perfect registration between both datasets, and the data quality still decreases during the cardiac cycle, just not as much.

To overcome this problem, the CMR tagging technique described above was developed to maintain high quality tagging information throughout the cardiac cycle wherein tagging pulses are applied asynchronously with the ECG trigger, adding a time-from-tagging sampling dimension to the dataset. This dimension is generated by applying the tag pulse at fixed intervals, or pseudo-randomly spaced intervals throughout the imaging acquisition. By tagging the images asynchronously with respect to the trigger pulse, each acquired k-space line is a discrete time from the cardiac trigger, and a discrete time from the tagging pulse. Because the tagging pulse is not played with the cardiac trigger, these two times can be, and are, different for most lines of k-space. The acquired data lines can then be re-binned according to when they were acquired in relation to the cardiac trigger as well as the tagging module. To reduce the amount of additional data required to sample this new data dimension, we apply a compressed sensing reconstruction suited for constraining both temporal directions. The reconstruction minimizes the L1 norm of the wavelet transform of the images in the x and y dimensions and minimizes the L1 norm of total variation in both the time from tagging and time from trigger dimensions. The reconstruction is performed iteratively until a solution is solved, using an alternating direction method of multipliers (ADMM) optimization scheme. We demonstrate that data reconstructed from asynchronously tagged CMR can be acquired with a novel sequence, and that the method produces constant tag-tissue contrast for all cardiac phases. The sequence allows the user to control the tagging interval, as well as any additional randomness added to the interval to make sure it stays asynchronous. The time from trigger, time from tagging, and respiratory position are all recorded by the sequence and logged to match with each acquired portion of k-space.

This technique may be used in place of traditional tagging sequences in the clinic. It allows for more consistent data quality through all phases of the cardiac cycle, leading to better data acquisition, and potentially easier post-processing. Additionally, because the sequence is binned retrospectively, it allows for free-breathing acquisitions, while the traditional methods require breath holding.

The time between triggers should be selected at approximately the T1 of the tissue being measured, so the previous set of tag lines have had appropriate time to relax and not contaminate the next set of tag lines. Additionally, the undersampling ratio can be selected to balance the scan time and allowable image artifacts, as well as determines the amount of regularization that should be applied in the compressed sensing reconstruction.

The sequence has been implemented for a standard grid-tagged and DENSE acquisition, and data acquired in a human volunteer.

In the following illustrative example, cardiac MRI (CMR) tagging is used to measure time-resolved myocardial motion. This motion data can be used to derive global (e.g. twist and torsion) or regional (e.g. strain and strain rate) measures that are important tools in the diagnosis of cardiac dysfunction, treatment monitoring, and in understanding the basic mechanisms of cardiac function. [13-14]

Methods

The asynchronously tagged sequence was developed and run in a healthy volunteer (IRB approved, consent obtained). The tagging pulses were played out at a fixed interval of 1250 ms, and the volunteers R-R interval was in the range of 650-800 ms during free breathing. Imaging data was acquired with a radial trajectory and tiny golden angle ordering (TE/TR=2.16/4.43, FA=14°, FOV=380 mm×380 mm×8 mm, resolution=1.7 mm×1.7 mm). Both a grid-tagged sequence (120° flip, 1-3-3-1 pulse, 8 mm spacing) and a phase-cycled DENSE encoded sequence (3-pt XY encoding, ke=0.08 cycles/mm) were implemented and scanned. Data was acquired with ~2× undersampling (grid-tag: 100,000 projections, 7 minutes), (DENSE: 140,000 projections, 10 minutes) and then retrospectively undersampled by selecting a number of spokes per phase. All data was acquired free-breathing and only 50% of the data in end expiration was used.

Figure 9:
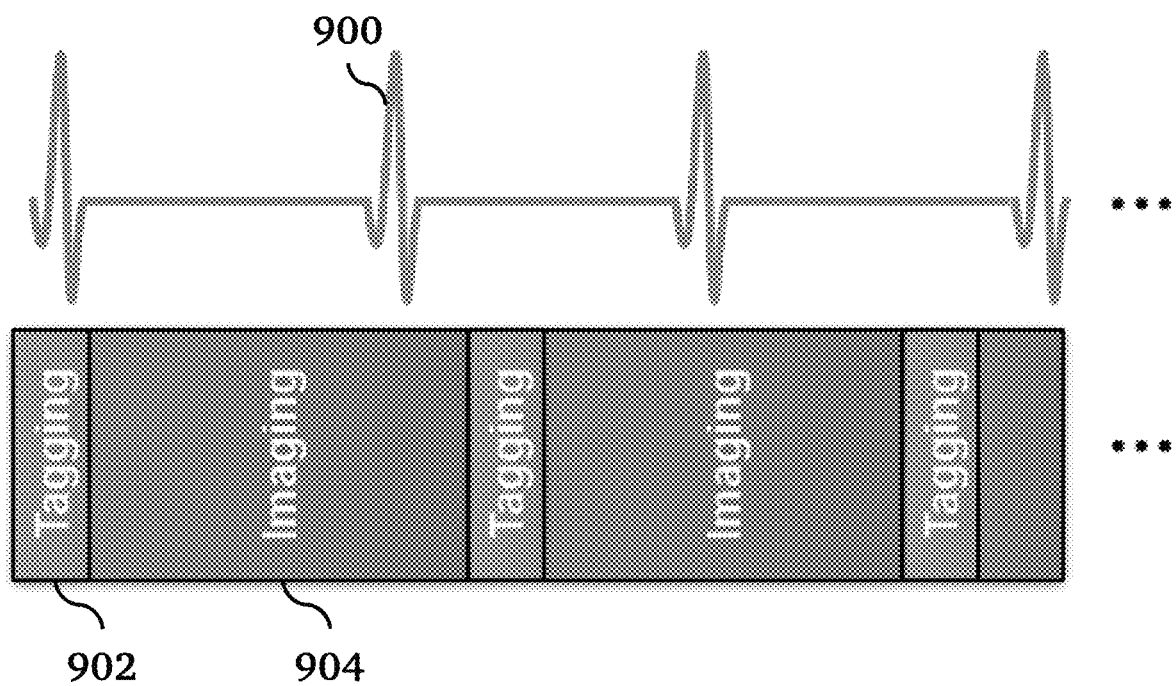
FIG. 9 shows a depiction of the tagging and imaging ordering scheme used in the acquisition, relative to the ECG signal, according to an embodiment of the invention.

FIG. 9 shows a depiction of the tagging 902 and imaging 904 ordering scheme used in the acquisition, relative to the ECG signal 900. The tagging and imaging are played out at fixed intervals, so that all cardiac phases are imaged both close and far from a tag pulse at different times in the sequence.

The data were reconstructed with a standard compressed sensing reconstruction, with a wavelet constraint in the two spatial dimensions ($\lambda$=0.001) and a total variation constraint in the cardiac and tagging temporal dimensions ($\lambda$=0.01), implemented with BART [17]. Data was binned for 20 phases in both temporal dimensions (400 total phases). Reconstructions were retrospectively undersampled to 8, 16, and 32 radial spokes per image, corresponding to free-breathing scan times of approximately 30, 60 and 120 seconds.

Results

Figure 10:
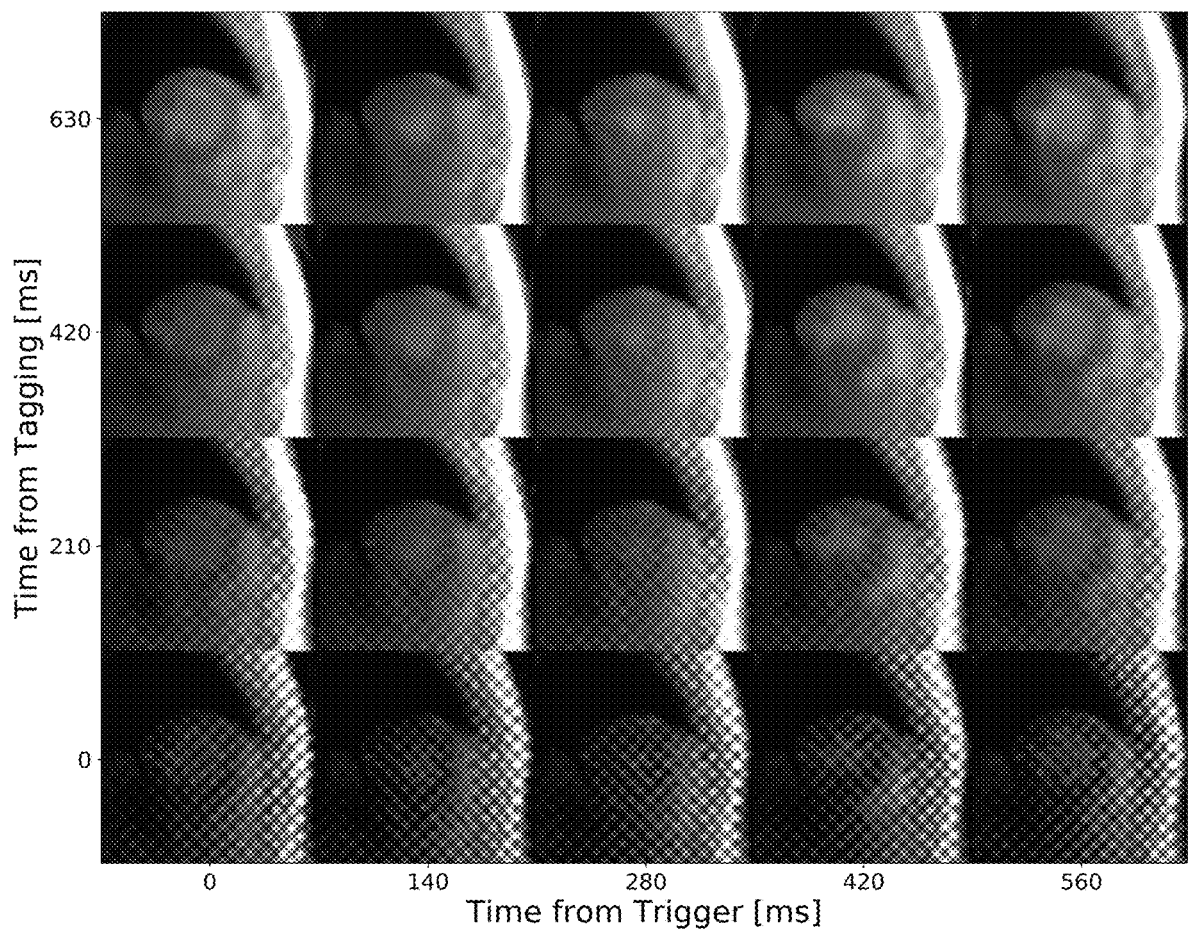
FIG. 10 shows the reconstructed phases of the 32 spoke-per-phase reconstruction for the grid-tagged data, according to an embodiment of the invention.
Figure 11:
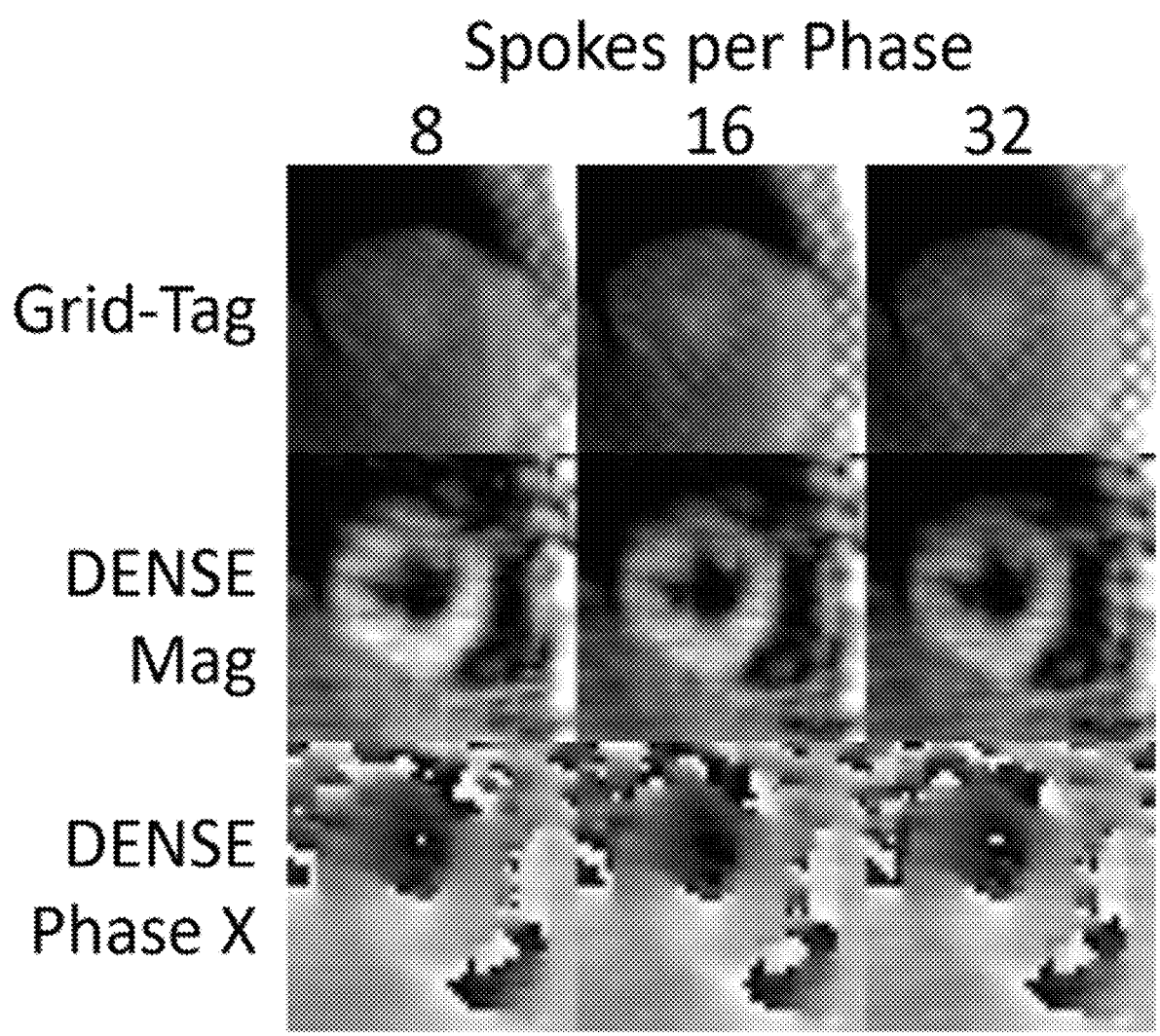
FIG. 11 shows example images from a single temporal phase with 8, 16, and 32 spokes per phase, according to an embodiment of the invention.

FIG. 10 shows the reconstructed phases of the 32 spoke-per-phase reconstruction for the grid-tagged data. Only a portion of phases are shown (5/20 cardiac, 4/20 tagging). The images show good quality tissue-tag contrast with constant data quality in the time-from-trigger temporal dimension (bottom row), which provides the first proof-of-concept of this approach. As expected, the tag quality decreases in the time-from-tagging dimension (columns). FIG. 11 shows example images from a single temporal phase (t_tag=210 ms, t_trig=210 ms) with 8, 16, and 32 spokes per phase, where reasonable data quality and tag contrast is seen (decreasing slightly with fewer spokes), reasonable quality was seen even with only 8 spokes per temporal phase. The rows show reconstructions with 8, 16, and 32 spokes per phase, for grid-tagged data, and DENSE magnitude and phase data.

Discussion

A new method of generating tagged CMR datasets was demonstrated where the tagging pulses are played asynchronously with the ECG trigger to sample both the time-from-trigger and time-from-tagging dimensions independently. This produces more uniform tag-tissue contrast for full cardiac cycle coverage. With multi-dimensional compressed sensing, good images can be acquired with ~16 radial projections, which requires <2 minutes of free-breathing per slice. The acquired data was reconstructed into both cardiac and tagging temporal dimensions with acceptable image quality. This work also presents the initial proof-of-concept for a novel approach to tagged CMR acquisition and reconstruction. Significant work, however, remains to determine the optimal acquisition parameters and the best method of combining all the cardiac and tagging phases together to provide optimal displacement and strain accuracy.

REFERENCES

[1] Young, A. A., Kraitchman, D. L., Dougherty, L. & Axel, L. Tracking and Finite Element Analysis of Stripe Deformation in Magnetic Resonance Tagging. IEEE Trans. Med. Imaging 14, 413-421 (1995).
[2] Prince, J. L. & Mcveigh, E. R. Motion Estimation from Tagged MR Image Sequences. IEEE Trans. Med. Imaging 11, 238-249 (1992).
[3] Gotte M J W, Germans T, Rüssel I K et al Myocardial strain and torsion quantified by cardiovascular magnetic resonance tissue tagging. Studies in normal and impaired left ventricular function. J Am Coll Cardiol (2006)
[4] Osman N F, Kerwin W S, Mcveigh E R, Prince J L Cardiac motion tracking using CINE harmonic phase (HARP) magnetic resonance imaging. Magn Reson Med 42 (6): 1048-1060 (1999)
[5] Ronneberger, O., Fischer, P. & Brox, T. U-net: Convolutional networks for biomedical image segmentation, in Lecture Notes in Computer Science (including subseries Lecture Notes in Artificial Intelligence and Lecture Notes in Bioinformatics) 9351, 234-241 (Springer Verlag, 2015).
[6] Nam, H. & Han, B. Learning Multi-domain Convolutional Neural Networks for Visual Tracking. in Proceedings of the IEEE Computer Society Conference on Computer Vision and Pattern Recognition 2016 December, 4293-4302 (2016).
[7] Verzhbinsky, I. A. et al. Estimating Aggregate Cardiomyocyte Strain Using In Vivo Diffusion and Displacement Encoded MRI. IEEE Trans. Med. Imaging (2019).
[8] McNally E M, Kaltman J R, Benson D W, Canter C E, Cripe L H, Duan D, Finder J D, Groh W J, Hoffman E P and Judge D P. Contemporary cardiac issues in Duchenne muscular dystrophy. Circulation. 2015; 131:1590-1598.
[9] Bushby K, Finkel R, Birnkrant D J, Case L E, Clemens P R, Cripe L, Kaul A, Kinnett K, McDonald C and Pandya S. Diagnosis and management of Duchenne muscular dystrophy, part 1: diagnosis, and pharmacological and psychosocial management. The Lancet Neurology. 2010; 9:77-93.
[10] Sadek, Abdelrahim Abdrabou et al. "Evaluation of cardiac functions in children with Duchenne Muscular Dystrophy: A prospective case-control study." Electronic physician vol. 9,11 5732-5739. 25 Nov. 2017, doi: 10.19082/5732
[11] Hor K N, Wansapura J, Markham L W, Mazur W, Cripe L H, Fleck R, Benson D W and Gottliebson W M. Circumferential strain analysis identifies strata of cardiomyopathy in Duchenne muscular dystrophy. Journal of the American College of Cardiology. 2009; 53:1204-1210
[12] L. E. Perotti, P. Magrath, I. A. Verzhbinsky, E. Aliotta, K. Moulin, D. B. Ennis "Microstructurally Anchored Cardiac Kinematics by Combining In Vivo DENSE MRI and CDTI" Functional Imaging and Modelling of the Heart, Toronto, Canada, June 2017
[13] Young A A Cowan B R JCMR 2012
[14] Jeung, Mi-Young, et al., Radiographics 2012.
[15] Cheng, J Y, et al., Scientific Reports 2017.
[16] Feng L, et al., MRM 2016.
[17] Tamir J I, et al. ISMRM Workshop Sedona 2016.

The invention claimed is:

1. A method for magnetic resonance imaging (MRI) tag tracking, the method comprising:
   synthetically generating synthetic tagged image data from natural images using programmed tag motion and a full Bloch simulation, wherein the synthetic tagged image data comprises dynamic training images and tag motion paths;
   providing the synthetic tagged image data to a convolutional neural network (CNN), wherein the CNN is configured to generate grid tag motion paths indicative of cardiac motion;
   acquiring MRI images using a tagged imaging method; and
   determining, based on the grid tag motion paths indicative of cardiac motion, a path of tag lines through a cardiac cycle from the MRI images,
   wherein generating the synthetic tagged image data comprises: applying periodic motion fields to the natural images to produce the dynamic training images, and generating tagged images from the dynamic training images using the full Bloch simulation, wherein the synthetic tagged image data are based on the tagged images.

2. The method of claim 1, wherein the convolutional neural network (CNN) includes both coordinate convolutions and (2+1)D convolutions.

3. The method of claim 1, further comprising determining, based on the grid tag motion paths, strain curves using strain tensor derivation.

4. The method of claim 1, wherein the tagged imaging method comprises applying tagging pulses asynchronously with an electrocardiogram (ECG) trigger, and including a time-from-tagging sampling dimension in tagged data.

5. A method comprising:
   generating, based on one or more natural images, synthetic tagged image data;
   providing the synthetic tagged image data to a machine learning model, wherein the machine learning model is configured to generate one or more grid tag motion paths indicative of cardiac motion;
   receiving one or more magnetic resonance imaging (MRI) images; and
   determining, based on the one or more grid tag motion paths and based on the one or more MRI images, one or more tag lines indicative of one or more motion paths throughout a cardiac cycle,
   wherein generating the synthetic tagged image data comprises applying one or more periodic motion fields to the one or more natural images to determine the one or more dynamic training images, and generating one or more tagged images from the one or more dynamic training images using a full Bloch simulation, wherein the synthetic tagged image data are based on the tagged images.

6. The method of claim 5, wherein the machine learning model is a convolutional neural network (CNN).

7. The method of claim 6, wherein the CNN comprises both coordinate convolutions and (2+1)D convolutions.

8. The method of claim 5, wherein the synthetic tagged image data comprises one or more dynamic training images and one or more tag motion paths.

9. The method of claim 5, wherein the one or more periodic motion fields are indicative of one or more physiological motion field or one or more non-physiological motion field.

10. The method of claim 8, wherein generating the synthetic tagged image data further comprises:
    randomly selecting the one or more natural images from a database; and
    determining, based on one or more points associated with the one or more natural images, the one or more tag motion paths.

11. The method of claim 5, further comprising determining, based on the one or more tag lines, one or more strain curves.

12. The method of claim 11, wherein the one or more strain curves are determined based on strain tensor derivation.

13. The method of claim 5, wherein receiving one or more MRI images further comprise:
    applying one or more tagging pulses asynchronously with an electrocariogram (ECG) trigger; and
    determining a time-from-tagging sampling dimension in tagged data.

14. A method comprising:
    providing synthetic tagged image data to a machine learning model configured to generate one or more grid tag motion paths indicative of cardiac motion, wherein the synthetic tagged image data are generated based on one or more natural images by applying one or more periodic motion fields to the one or more natural images to determine the one or more dynamic training images, and generating one or more tagged images from the one or more dynamic training images using a full Bloch simulation, wherein the synthetic tagged image data are based on the tagged images; and
    determining, based on the one or more grid tag motion paths and based on one or more MRI images, one or more tag lines indicative of one or more motion paths throughout a cardiac cycle.

15. The method of claim 14, wherein the machine learning model is a convolutional neural network (CNN).

16. The method of claim 14, wherein the synthetic tagged image data comprises one or more dynamic training images and one or more tag motion paths.

17. The method of claim 14, further comprising determining, based on the one or more tag lines, one or more strain curves using strain tensor derivation.

18. The method of claim 14, wherein receiving one or more MRI images further comprise:
    applying one or more tagging pulses asynchronously with an electrocardiogram (ECG) trigger; and
    determining a time-from-tagging sampling dimension in tagged data.

\* \* \* \* \*